US00PP36892P2

(12) United States Plant Patent
Rodrigues et al.

(10) Patent No.: US PP36,892 P2
(45) Date of Patent: Aug. 19, 2025

(54) PINEAPPLE PLANT NAMED 'FR3593W'

(50) Latin Name: *Ananas comosus*
Varietal Denomination: FR3593W

(71) Applicant: Del Monte International GmbH, Zug (CH)

(72) Inventors: Joao Rodrigues, Limoeiro do Norte (BR); Hans Sauter, Coral Gables, FL (US); Ebrahim Firoozabady, Pleasant Hill, CA (US)

(73) Assignee: Del Monte International GmbH, Zug (CH)

( * ) Notice: Subject to any disclaimer, the term of this patent is extended or adjusted under 35 U.S.C. 154(b) by 0 days.

(21) Appl. No.: 18/816,953

(22) Filed: Aug. 27, 2024

(51) Int. Cl.
*A01H 5/08* (2018.01)
*A01H 6/22* (2018.01)

(52) U.S. Cl.
USPC ..... Plt./156

(58) Field of Classification Search
USPC ..... Plt./156
See application file for complete search history.

*Primary Examiner* — Susan McCormick Ewoldt
(74) *Attorney, Agent, or Firm* — Dickinson Wright PLLC; Kristopher Lance Anderson

(57) ABSTRACT

A new and distinct pineapple plant named 'FR3593W', comprising certain unique traits, standing out *Fusarium* resistance obtained after crossing and backcrossing *Fusarium* resistant pineapple lines with an MD-2 pineapple. The invention incorporates stable, inheritable resistances to *Fusariosis* disease in a pineapple variety capable of addressing all of the high-quality requirements of Latin American and other consumer markets.

6 Drawing Sheets

Genus and species: *Ananas comosus.*

Variety denomination: 'FR3593W'.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

Inventors: Joao Rodrigues, Hans Sauter, and Ebrahim Firoozabady.

BACKGROUND OF THE NEW PLANT

The present invention comprises a new and distinct pineapple variety of *Ananas comosus*, hereinafter referred to as the variety named 'FR3593W'. The said variety has been developed by sexual crossing between plants of EC-120 variety (non-patented) and the variety 'MD-2' (non-patented) and selected from large populations of progenies of hybrids (F1), backcrossed two times with MD-2 (BC1 and BC2). This process started in 2009 in Limoeiro do Norte, Ceará, Brazil, and took fifteen consecutive years of iterative hybridization, selection, and planting. The new variety 'FR3593W' in particular was the result of the back-cross of a selected plant of the '1/2.63' line, with a selected plant of 'MD-2', to achieve the combination of characters of interest that qualify 'FR3593W' as a variety of commercial potential. The 1/2.63 line corresponds to the first backcross (BC1) of the selected F1 hybrid (code 19140) with MD-2. The F1 hybrid originated from the initial cross between MD-2 and EC-120 in 2012. The first backcross (BC1) was performed in 2015, using 19140 as the male parent crossed with MD-2. Subsequently, the FR3593W variety resulted from a second backcross (BC2) in 2019, where the 1/2.63 line was further crossed with MD-2. This process aimed to reinforce the desirable traits of MD-2 while maintaining the resistance to *Fusarium guttiforme* inherited from EC-120.

The main objective of the hybridization program was to introduce stable resistance to *Fusariosis* disease of pineapples into a variety that would produce attractive fruits with excellent organoleptic traits and the right shape and size that would satisfy the strict requirements of Latin American and other consumer markets. The new cultivar 'FR3593W' is being reproduced asexually faithful to the type in Limoeiro do Norte, Ceará, Brazil through the tissue culture technique.

BACKGROUND INFORMATION ABOUT THE DISEASE

Among all the diseases of pineapple (*Ananas comosus* var. *comosus*), *Fusariose caused* by *Fusarium guttiforme* stands out for being the one that brings largest economic losses to producers, with estimated losses between 50% and 100% of fruits and up to 50% in propagules (Matos, 2008).

*Fusarium guttiforme* can infect all parts of the pineapple causing the exudation of a gummy substance from the affected tissues. In plants, the lesion is located on the stem and progresses to the base of the leaf being restricted to the achlorophyllous region. Under field conditions an infected pineapple plant may show one or more external symptoms: stem tilt to the side where the lesion is located; changes in plant phyllotaxis, increasing the number of leaves per spiral; changes in the architecture of the plant that has the appearance of a funnel or cup; reduction in leaf length as well as in the overall development of the plant; "opening" of the central rosette of plants showing the youngest leaves; reducing the stem development; chlorosis; death of the apical meristem. As the disease progresses, the plant paralyzes growth and dies (Matos & Junghans, 2006).

In the fruits, the symptoms are manifested in the form of soft rot in the pulp, with accumulation of gum in the ovules of the ovary and exudation of the same through the infected floral cavity. At a more advanced stage of disease development, the skin of the fruit in the infected areas presents a red brown coloration and are at the lower level. These symptoms are observed with greater intensity in fruits near harvest (Matos & Junghans, 2006).

Following extensive field and laboratory research, four isolates of *Fusarium guttiforme* were identified for their particularly high virulence in the North East of Brazil, subsequently isolated and reproduced to serve as standard inoculum for the resistance trials the pineapple hybrids participating in this project were subjected to.

SUMMARY OF THE INVENTION

The invention is related to a new and distinct pineapple variety of the Bromeliaceae family, which was derived from a backcross (BC2) between the 'MD-2' and the '1/2.63' (which in turn was already a backcross of a backcross between 'MD-2' X 'EC-120' cultivar), wherein the MD-2 variety was used as the female parent, while the lines obtained from the backcrosses were used as the male parent. The new and distinct pineapple variety was derived through hand pollination and mass selection process during fifteen years and provides *Fusarium* resistance to pineapple plants that could be grown in all areas, including where the disease caused by *Fusarium guttiforme* occurs.

In most characteristics, the selected hybrid is more alike to the 'MD-2' parent than the '1/2.63' parent. The main difference is in the resistance to *Fusarium guttiforme* exhibited by the 'FR3593W' and absent in the 'MD-2' variety. The selected backcross 2 (BC2) plant's fruit has an internal quality and pulp color pale white which also differentiates it from 'MD-2' fruit: the total soluble solid contents (TSS), citric acid, ascorbic acid, and the size of the fruit are like the 'MD-2'. In addition, the 'FR3593W' fruit is cylindrical in shape, and has a very pleasant aroma, and delectable taste, just like the 'MD-2' variety.

Applicant has previously filed for patent for FR11834 with U.S. Plant Pat. No. 35,670 P2on Mar. 5, 2024, another *Fusarium* resistant varieties produced of this program, however, in contrast to that said variety, 'FR3593W' exhibits pale white to beige color pulp. The new variety is characterized by longer and thinner leaves, and the occasional presence of spines at the leaf tip. Leaf color is gray-green, similar to the color of both parental lines, 'MD-2', and the BC1 'EC120' hybrid '1/2.63' (FIG. 1).

BRIEF DESCRIPTION OF THE PHOTOGRAPHS

The accompanying pictures illustrate the overall appearance of the new *Ananas comosus* var. *comosus* 'FR3593W' showing infection damage caused by artificial inoculation with four different isolates of *Fusarium guttiforme* showing the colors as reasonably possible with colored reproductions of this type. The lesion caused by direct inoculation with an infected needle on the fruit helped verify the resistance trait (earlier established by immersion of young plants in a suspension of *Fusarium guttiforme*'s most virulent isolate), when comparing reaction of fruit pulp tissue of the new pineapple variety 'FR3593W' with 'MD-2':

DETAILED BOTANICAL DESCRIPTION

Figure 1:
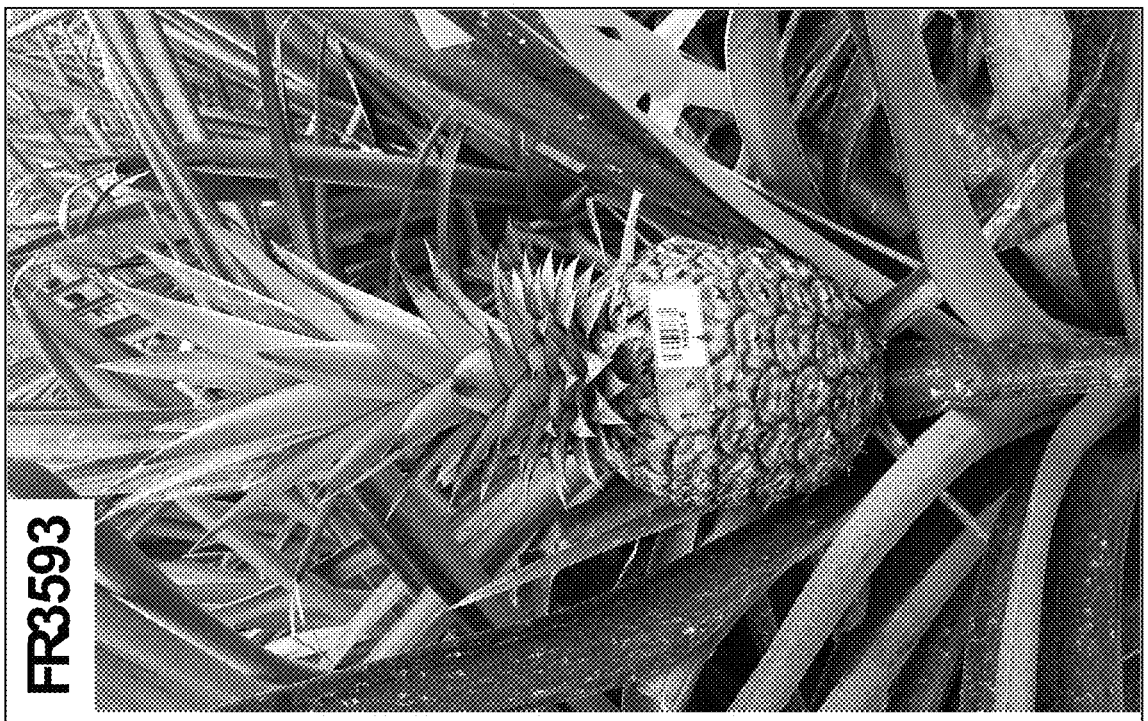
FIG. 1 depicts a view of the new variety 'FR3593W' at 4.8 months after forcing (MAF).
Figure 2:
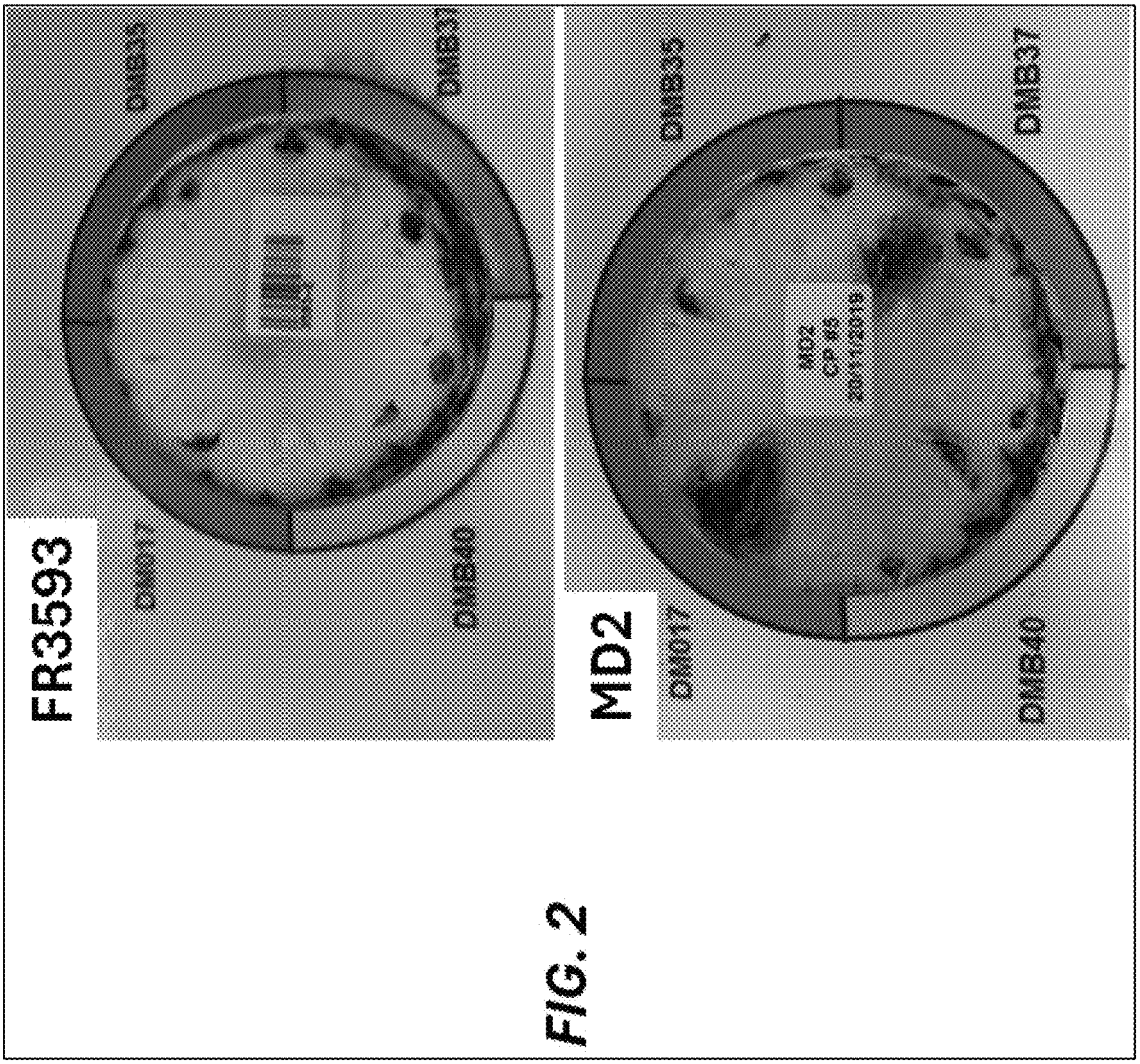
FIG. 2 depicts a cross sectional view of 'FR3593W' and 'MD-2' fruit inoculated with *Fusarium guttiforme* isolates DM017, DMB35, DMB37 and DMB40 at 4.8 MAF.
Figure 3:
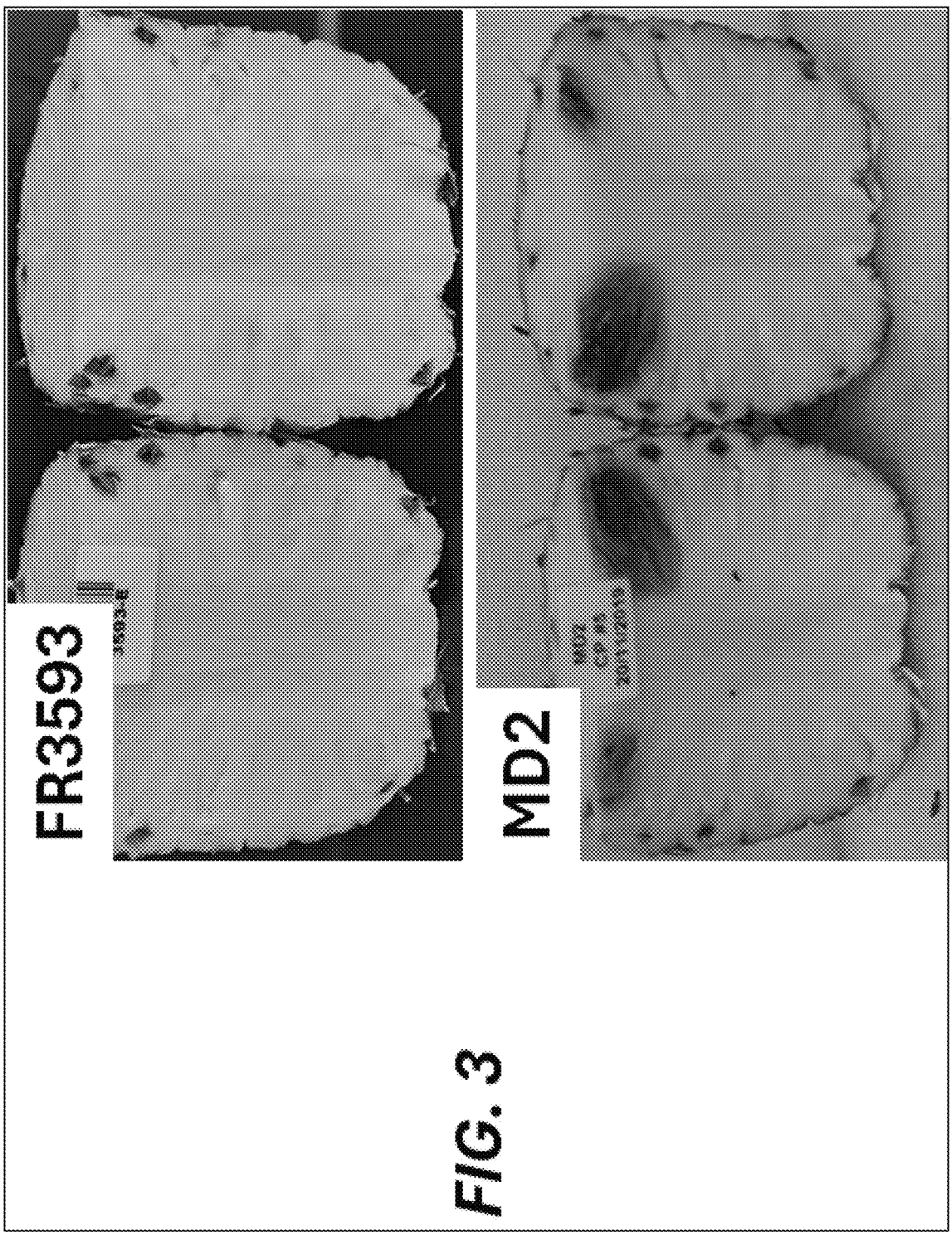
FIG. 3 depicts a longitudinal section view of *Fusarium guttiforme* inoculation site on fruit of 'FR3593W' variety and 'MD-2' fruit at 4.8 MAF.
Figure 4:
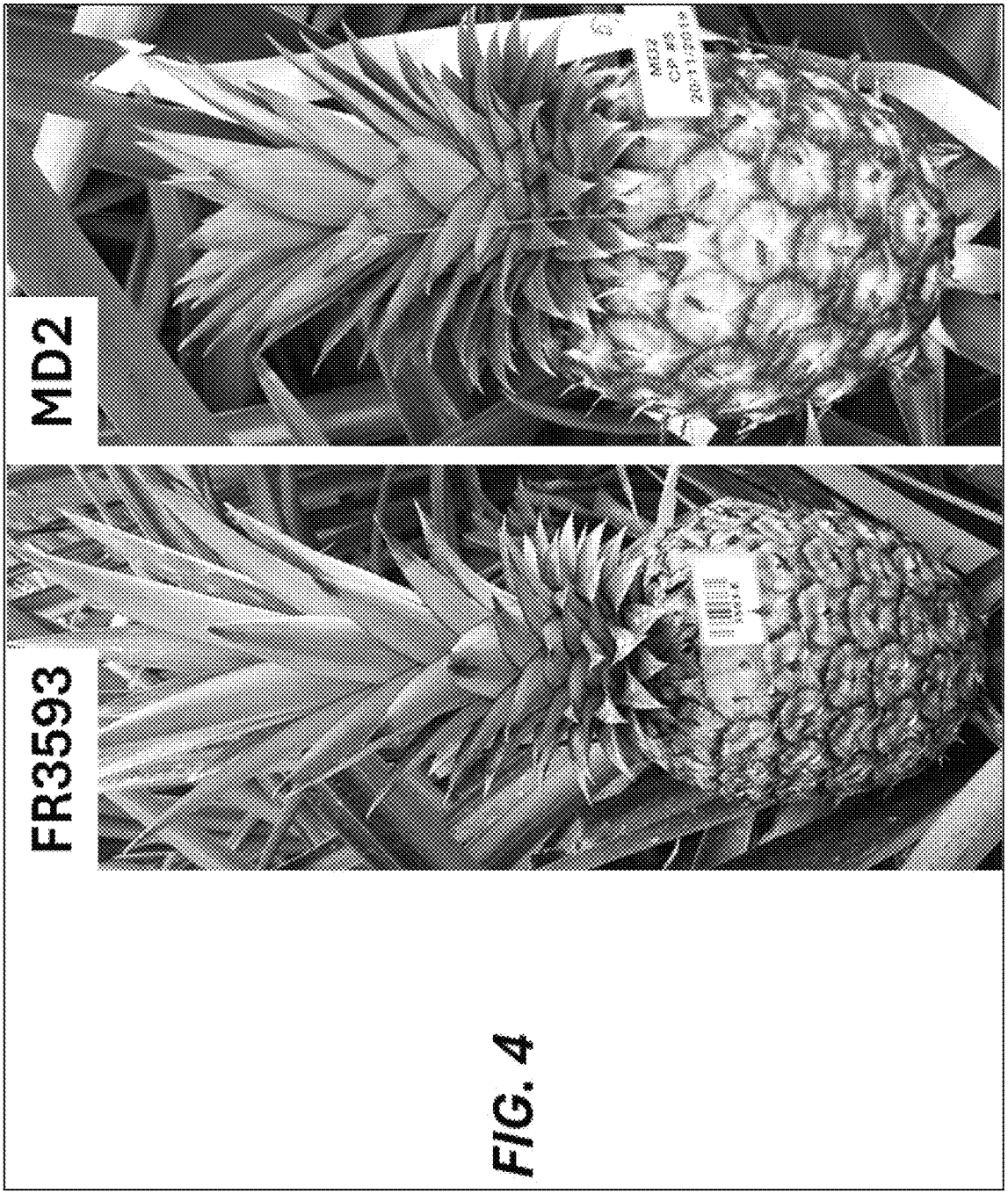
FIG. 4 depicts an external view of *Fusarium guttiforme* inoculation site on fruit of 'FR3593W' and MD-2 varieties at 4.8 MAF.
Figure 5:
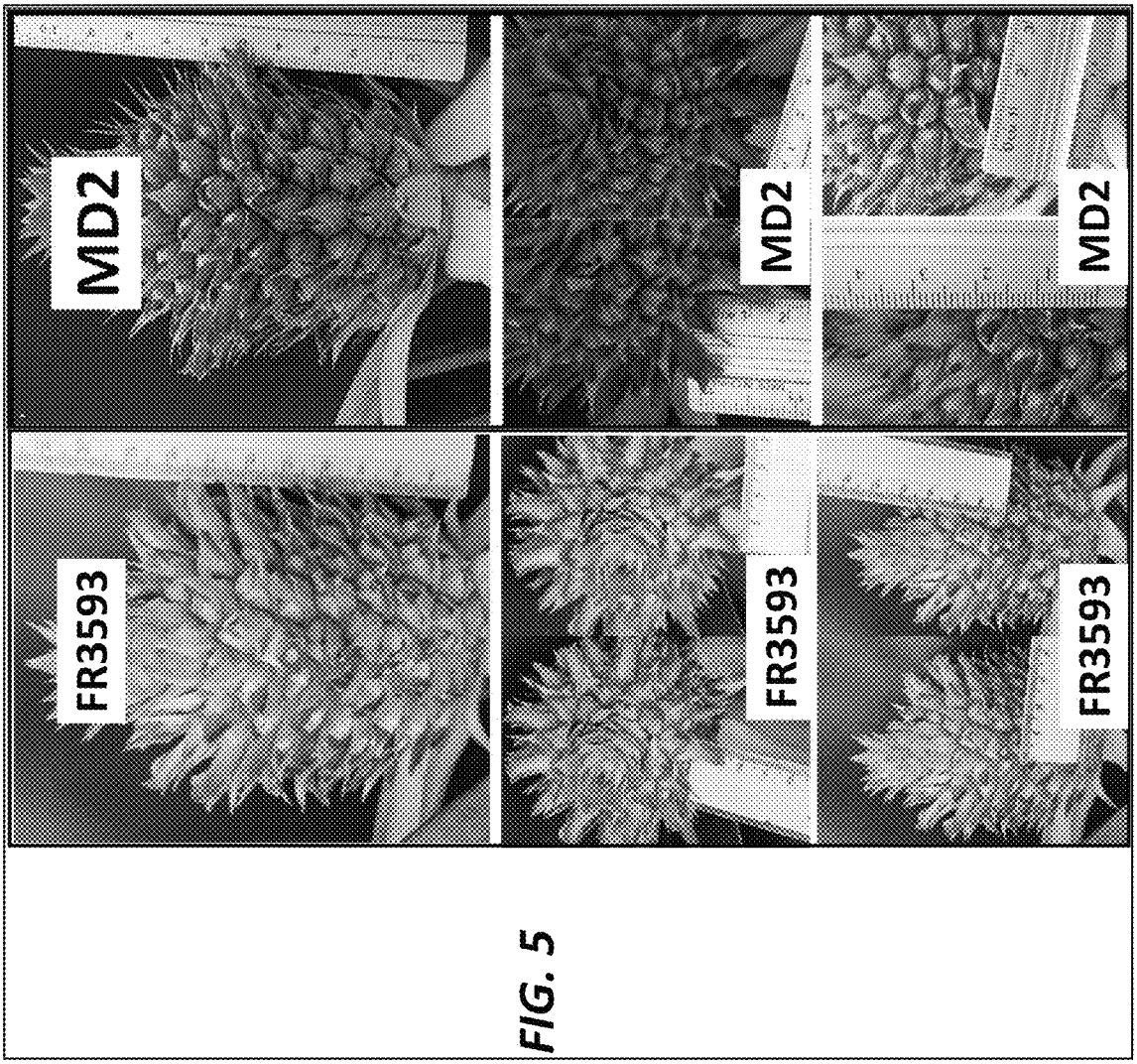
FIG. 5 depicts an external view of inflorescence of 'FR3593W' and MD-2 varieties at 61 days after floral induction.
Figure 6:
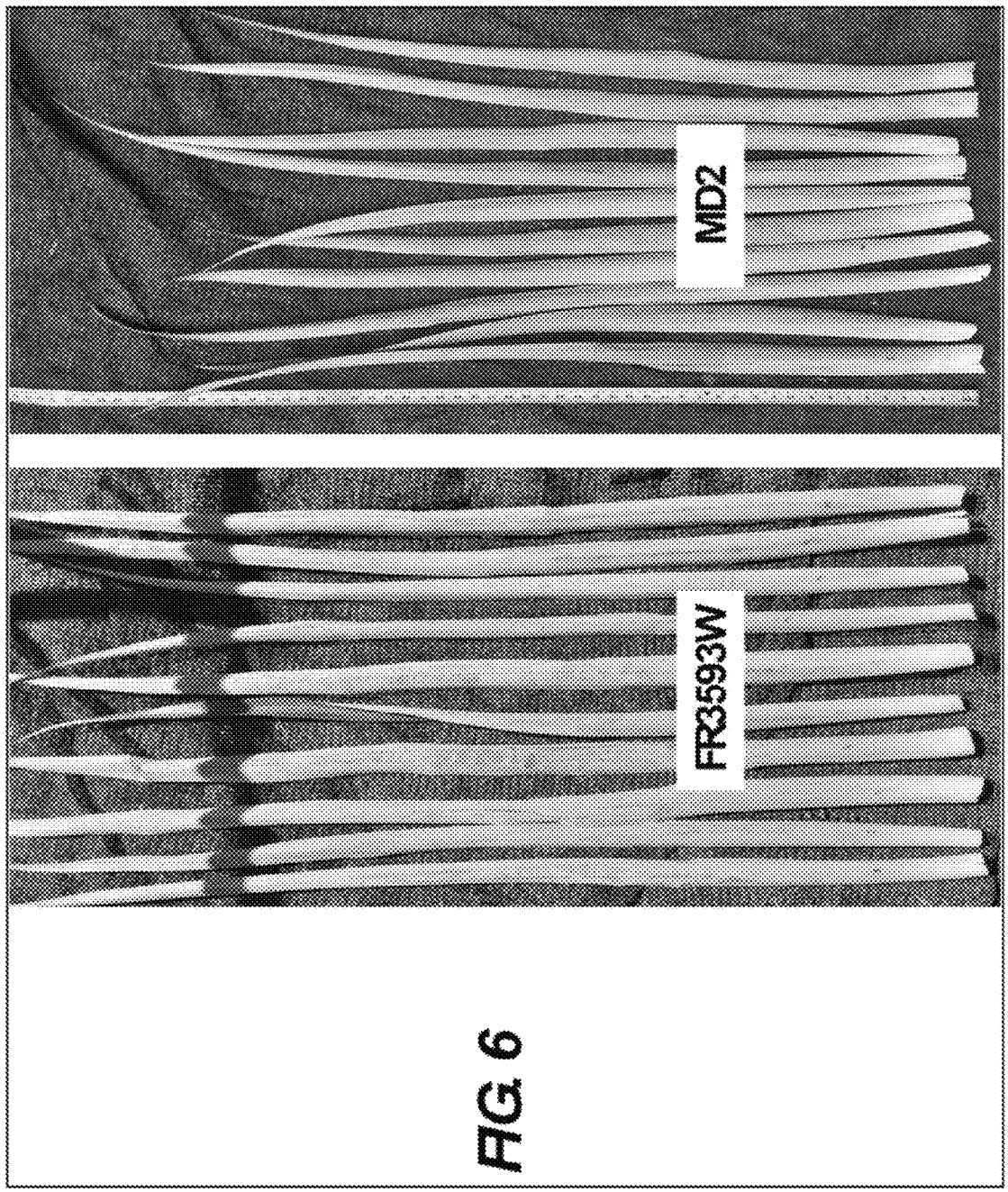
FIG. 6 depicts an external view of 'FR3593W' plants with exhibited tall stature, with longer and more channeled leaves compared to the leaves of the MD-2 varieties.

The new *Ananas comosus* cultivar 'FR3593W' has not been observed under all possible environmental conditions. However, the plants were grown under environmental conditions and cultural practices which approximate those generally used in commercial pineapple growing operations. The phenotype of the new cultivar may still vary depending on the environmental conditions such as temperature, humidity, light intensity, and photoperiod without any change made to the genotype of the plant.

The aforementioned photographs, together with the following observations, measurements and values describing plants of 'FR3593W' variety are based on observations made under optimally fertilized and growing conditions, in the region of Limoeiro do Norte, Ceará, Brazil (latitude −5.21945833° and longitude −37.914505°, where the temperatures generally range from 15.96-38.70° C., and an annual rainfall average of 746 mm.

The color terminology and designation reported here are in accordance with the Munsell Color Notation for Plants Tissues published by Munsell Color Macbeth, a division of Kollmorgen Corporation, Baltimore, Md. USA.

The following description was made based on a population of 'FR3593W' plants, the BC2 hybrid obtained through hand pollination of parental lines in 2015 and planted in 2017 and fruit harvested in 2019 and new propagules produced from this plant planted in 2019.

Plant identification: Name: *Ananas comosus* var. *comosus* 'FR3593W'.

Parental Lines: Selected plant BC1 '1/2.63' backcrossed to 'MD-2'.

Origin: Conventional genetic improvement (hand pollination), through crossing and backcrossing.

Classification: Botanical: Bromeliaceae or pineapple family. Subfamily: Bromelioidae. Genus: *Ananas*. Subgenus: *comosus*. Variety: 'FR3593W'.

Commercial: Bromeliad fruit plant (pineapple).

Form: Terrestrial (in plantation), with overlapping, sessile leaves from a funnel-formed rosette, surrounding a composite inflorescence (during anthesis), with few or no slips in the fruit peduncle and suckers that are produced in the stem and originate subsequent crops.

General description: 'FR3593W' (before anthesis).

Growth habit: Semi-erect, with an average plant height of 168 cm.

Stem:

I. *General*.—Short, vertical, and covered by overlapping leaves, each leaf with a dominant axillary bud.

II. *Stem texture*.—Glabrous and fleshy,

III. *Stem size*.—A) Length (above soil level): usually between 13.90-26.00 cm at anthesis. B) Diameter between 6.90-14.00 cm at ground level to the anthesis.

IV. *Stem shape*.—Cylindrical and with a narrower diameter at the distal part.

V. *Stem color*.—Whitish in color (5Y 7.8/2.3 in the Munsell color chart).

Leaves:

I. *General*.—Closely overlapping sessile leaves (formed in acropetal succession) forming a dense rosette, the outline of which in longitudinal section is roughly heart shaped. The number of leaves fluctuates between 42-56 with a 5/13 phyllotaxy.

II. *Texture*.—A) Upper epidermal area: Glabrous, semirigid and channeled (or concave) except at the leaf tip. B) Lower epidermal area: Finely striated (longitudinally) and appears covered with a white layer consisting of scale like trichomes.

III. *Leaf arrangement*.—Alternate and in rosette shape.

IV. *Leaf margins*.—Entire margin, with rarely found irregularly spaced small deltoid cuspidate hooked spines usually located on the distal portions of leaves. Size of spines 0.50-0.95 mm.

V. *Leaf venation*.—Parallel.

VI. *Leaf shape*.—Leaves are not uniform in shape and vary with the position of the leaf on the stem. The basal or oldest leaves are lanceolate while the base is considerably expanded. There is a noticeable narrowing in width between achlorophyllous (basal) and chlorophyllous (or main portion) of the leaves. The longest or most mature leaves are lanceolate in shape, but the base is without the arcuate expansions of the preceding leaves. The remaining leaves (or center leaves of the plant rosette) are lanceolate in form with no expansion of width into the base. The leaf apex is acuminate.

VII. *Leaf size* (*to anthesis*).—A) Length: Usually between 138.0-155.0 cm for those 'D' leaves with a non chlorophyllous base that usually is between 9.0-13.0 cm in length. B) Width: Normally between 5.9-8.5 cm in the mid leaf area of the longest leaves. The expanded basal disk usually has a maximum width of 6.7-12.4 cm. C) Thickness: In the longest leaves, it usually varies between 2.0-3.0 mm at the center of the mid leaf area and decrease laterally between 0.9-1.9 mm at the margin, while becoming slightly thinner towards the tip. The expanded basal disk at the mid stem area usually has a maximum thickness of 2.5-3.7 mm at the center of the blade and tapering laterally toward margins up to 1.2-1.9 mm.

VIII. *Leaf color like 'MD-2', mostly lacking anthocyanin*.—A) Upper epidermal surface: 1. General: dominant color is usually dark green. The color of the basal disk is predominantly white and light green; achlorophyllous basal disk area is commonly pale white. Mid leaf area: commonly dark green (4GY 5.5/5.2 in the Munsell color chart). Leaf tip area: commonly dark green (4GY 5.5/5.2 in the Munsell color chart). B) Lower epidermal surface (underside): General: commonly grayish green (6GY 7.8/1.4 in the Munsell color chart) with pale white basal disk area (5Y 8.0/3.8 in the Munsell color chart).

Inflorescence (at anthesis):

I. *General*.—Flower composite from 65-107 fruitlets borne per inflorescence of a long peduncle of approximately 10.0-27.8 cm length at the apical meristem. Individual bisexual flowers that consist of three Sepals, Six Stamens, three Stigmas and three Carpels. The inflorescence is self-incompatible producing edible fruit parthenocarpically (production of fruit without fertilization of ovules).

II. *Texture*.—Glabrous and fibrous.

III. *Shape*.—Oval with slightly raised flowers with a light red to grayish red color in the crown.

IV. *Size and color*.—Comparable to specimens of *Ananas comosus* var. *comosus*. Petal size: 1.4-1.7 cm. Petal color in the apex: light purple (1RP 4.6/10.5 in the Munsell color chart).

V. *Sepal size*.—0.53-1.03 cm. Sepal color: yellowish brown (1YR 7.4/1.4 in the Munsell color chart).

VI. *Floral bracts length*.—From 1.61-2.20 cm, serrated margins (with tiny spines); yellowish brown color (6R 6.0/11.5 in the Munsell color chart).

Crown (at harvest):

I. *General*.—Visually one crown. Visually one crown, composed on average of 69-103 leaves. Crown leaves are short, lanceolate in shape and erect at anthesis, measuring of 5.5-7.2 cm.

II. *Leaf arrangement*.—Alternate and in rosette shape.

III. *Leaf margins*.—Entire with smooth borders. Seldom very small spines in the tip of one leaf.

IV. *Size at harvest*.—Average 22.1-32.8 cm. Weight: average 229-345 g. Diameter: 11.5-17.2 cm.

V. *Shape*.—Medium crown with medium width and semirigid leaves, with the crown normally not exceeding length nor width of fruit and with semirigid leaves.

VI. *Attitude*.—Upright.

VII. *Color of the terminal crown leaves*.—A. Upper surface: Dark green color at the apex (5GY 2/2 in the Munsell color chart) and dark green at the base (6GY 4.6/5.1 in the Munsell color chart). B. Lower surface: grayish green (6GY 7.8/1.4 in the Munsell color chart).

Fruit (at harvest):

I. *Size*.—Usually with a weight between 709-1,863 grams and average weight of 1,214 grams. Fruit core's diameter 2.70-3.80 cm. Fruit core's color: pale white (8Y 6.7/2.2 in the Munsell color chart).

II. *Shape*.—Cylindrical with flat and medium size fruitlets. Medium crown (the length nor width of fruit) with thin and semirigid leaves. Fruit's height 9.20-14,50 cm, fruit's diameter: 8.00-11.60 cm.

III. *How borne*.—The development of the fruit occurs from the apical meristem of the plant on a long peduncle, usually between 10.00-27.80 cm length. No slips available for evaluation. 6 long peduncle bracts, with spines on the edges and of medium green to dark green color (3GY 7.3/3.7 in the Munsell color chart) are generally present at the base of the fruit.

IV. *Color*.—A) Shell: commonly grayish green at early maturity (6GY 3.9/6.7 in the Munsell color chart), with yellowish brown bract (6R 6.0/11.5 in the Munsell color chart). Fruit with pale white peduncle (5Y 6.0/2.0 in the Munsell color chart).

V. *Fruit flesh*.—Dense, firm, medium in fiber and juiciness, emitting characteristic pineapple aroma; flesh color distinctly pale white to beige (8Y 6.7/2.2 in the Munsell color chart).

VI. *Brix*.—Typically, 13.3-17.9 degrees, standing out from their parents.

VII. *Total acid levels*.—Usually between 0.27-0.83 milligrams of citric acid/ml of juice.

VIII. *Vitamin C content reported as ascorbic acid content*.—Regularly between 28.46-60.85 mg/100 ml of juice.

IX. *Plant/fruit resistance/susceptibility to pest and diseases*.—The plant of the new variety 'FR3593W' performs very similar to 'MD-2' differentiating mainly in its resistance to *Fusarium guttiforme*. Table 2 shows the comparison of pineapple varieties 'FR3593W', 'MD-2' and 'Champaka' (not patented) and their resistance to *Fusarium guttiforme*.

Others:

I. *Fertility*.—This plant is self-incompatible. This is the reason why the presence of sexual seeds is almost null. The material used for planting are suckers, fruit crowns and vitroplants.

II. *Vigor*.—This plant exhibits similar vigor as its parents, the '1/2.63' line, and the 'MD-2' variety.

III. *Yield*.—A population of this pineapple can have an agronomic yield from 89-112 ton/ha.

IV. *Plant use*.—The fruit will be commercialized within the fresh fruit and processed fruit for the local and export market. Shipping conditions are typically set as 14 days at 7 degrees, Celsius.

Summary of the special characteristics: the 'FR3593W' plants present the following differences when compared to its parental lines (MD-2) and known commercial lines (Pérola):

A. Resistance to *Fusarium guttiforme*; parental line MD-2 (and additionally non-parental line Pérola) is very susceptible to this pathogen, while 'FR3593W' exhibits total resistance.

B. Higher ascorbic acid content compared to the Pérola variety, generally range between 15 to 35 mg/100 g of fresh pulp.

C. Lower pulp porosity compared to the Pérola variety.

D. Pale white colored pulp: the backcross between the '1/2.63' backcross and 'MD-2', ended up in a combination of a fruit with shell color and pale white pulp different the 'MD-2' variety.

E. B. Longer and thinner leaves, ranging in length from 97.0 to 175.0 cm, compared to the MD-2 variety. Plant with little or none slips: 'MD-2' variety produces between 1-3 slips per plant, and the '1/2.63' produces between 0-1 slips per plant. By comparison, 'FR3593W', which reduces cosmetic and pest problems that can be originated by the contact of the slips with the fruit.

F. At full maturity, the resistance to *Fusarium guttiforme* allows the FR3593W to be harvested at the optimal point of ripeness, which permits consistently high sugar content and Brix levels similar to the MD-2 variety under similar conditions. The levels of citric acid and ascorbic acid are lower than those of MD-2, as well as the '1/2.63' fruit ratio.

G. As a result of the backcross process. 'FR3593W' has acquired resistance to *Fusarium guttiforme*, just like the '1/2.63' but with an improved fruit size and internal quality similar to the 'MD-2' highlighting the difference in pulp color. This combination of characteristics is important to differentiate this hybrid from its parents; as shown on Table 3, when reproduced asexually, these characteristics are stable and reproducible for successive generations.

TABLE 1

Average data for select organoleptic parameters and fruit size of the 'FR3593W' hybrid.

| Generation | n | Brix | Ascorbic Acid (mg/100 ml) | Citric Acid (mg/ml) | Fruit Weight (g) | Number of slips |
|---|---|---|---|---|---|---|
| 'FR3593W' | 48 | 15.09 | 38.95 | 0.64 | 1,214 | 0 |
| 'MD-2' | 71 | 16.3 | 61.4 | 0.95 | 1,949 | 0 |

(data for 'FR3593W' represent observations from evaluated when backcrossing 'MD-2' with 1/2.63 hybrid; data for 'MD-2' represents the average score for 'MD-2' variety in the region).

Individual plant description: The following is an overview of 'FR3593W' hybrid, a new pineapple plant variety, that was developed through hybridization process in Limoeiro do Norte, Ceará, Brazil.

*Plant age*.—17.22 months after planting plus 4.83 months after forcing.

*Plant growth habit*.—Semi-upright.

*Plant diameter*.—Between 142-165 cm between opposite leaf tips.

*Plant height*.—154-168 cm above ground surface.

*Stem*.—Length. Between 12.0-20.0 cm above ground sur-face. Diameter. Between 6.0-7.2 cm above ground surface.

Leaves:

I. *Number*.—42-56 leaves.

II. *Length*.—138-155 cm the longest leaf.

III. *Width*.—(Largest leaves) at mid leaf between 3.0-5.0 cm. Leaf piping is absent.

IV. *Thickness*.—2.0-3.0 mm along the axis.

V. *Color*.—A) Upper epidermal chlorophyllous area: Commonly dark green (4GY 5.5/5.2 in the Munsell color chart). B) Upper epidermal non chlorophyllous area: commonly pale white (5Y 8.0/3.8 in the Munsell color chart). C) Lower epidermal area: Commonly grayish green (6GY 7.8/1.4 in the Munsell color chart). Leaf anthocyanin coloration may appear slightly on some plants.

Inflorescence:

*General*.—Composite inflorescence borne on a long peduncle at the apical meristem. The inflorescence is composed of 65-107 flowers, which eventually lead to an equal number of fruitlets.

TABLE 2

Petals: Description of size and texture of flowers of 'FR3593W' hybrid

| Inflor-escence | ID | Trait | Note |
|---|---|---|---|
| | 14 | Size of bracts (cm) | 1.61-2.20 |
| | 15 | Petal: color of apex (purple red), base (white) | 2 |
| | 16 | Petal length (mm) | 14-17 |
| | N/A | Petal width (cm) | 0.60-0.70 |

TABLE 2-continued

| Petals: Description of size and texture of flowers of 'FR3593W' hybrid | | | |
|---|---|---|---|
| Inflor-escence | ID | Trait | Note |
| | N/A | Petal Height (cm) | 1.4-1.7 |
| | N/A | Petal texture | very finely textured and smooth feel |

TABLE 3

| Reproductive organs. Description of size and shape of reproductive organs of 'FR3593W' hybrid. | | |
|---|---|---|
| | Trait | Note |
| Inflor-escence | Style (mm) | 10.3-13.4 |
| | Stamen (mm) | 9.2-12.4 |
| | Style shape | tubular |
| | Stamen shape | tubular |
| | Style color | Base = white, top - pale purple |
| | Filament color | Filament base = white, filament top - pale purple |
| | Anther color | Pale yellow |
| | Pollen color | transparent |

TABLE 4

| Peduncule: length and diameter of the peduncle of 'FR3593W' hybrid are as follows. | | | |
|---|---|---|---|
| Peduncule | ID | Trait | Note |
| | 21 | Length (cm) | 10.0-27.8 |
| | 22 | Diameter (cm) | 2.2-3.5 |

TABLE 5

| Susceptibility to pest and diseases of different commercial varieties to *Fusarium guttiforme* ('FR3593W' is resistant and 'Champaka' and 'MD-2' are susceptible). | | | |
|---|---|---|---|
| | Pineapple Variety | | |
| Pest/Disease | 'FR3593W' | 'MD-2' | 'Champaka' |
| *Fusarium guttiforme.* | R+ | S+ | S |

The pineapple variety 'FR3593W' has a post-harvest shelflife similar to 'MD-2' variety, showing similar performance in shell dehydration studies.

'FR3593W' fruit general characteristics are as follows (A) a fruitlet apex which is flat; (B) the flesh density is medium; (C) the number fruitlets per syncarp is 65-107; (D) the fruitlet characteristics are as follows:

TABLE 6

| | ID | Trait | Note |
|---|---|---|---|
| Fruit | 31 | Fruit shape (cylindrical) | 3 |
| | 32 | Fruit length (cm) | 9.2-14.5 |
| | 33 | Fruit diameter (cm) | 8.00-11.60 |
| | 34 | Predominant color of mature eye (medium yellow) | 6 |
| | 35 | Fruit: Size (medium) | 5 |
| | N/A | Size of eye diameter width (cm) | 2.4-2.7 |
| | N/A | Size of eye length (cm) | 2.4-2.7 |

TABLE 6-continued

| ID | Trait | Note |
|---|---|---|
| N/A | Color of immature eye (grayish green) | 4 |
| 37 | Fruitlet apex (flat) | 2 |
| 38 | Evenness of color of eyes (even or slightly uneven) | 1 |

I. *Shell color*.—'FR3593W' shell color at mature (8Y 6.9/9.6 in the Munsell color chart) and immature (6GY 3.9/6.7 in the Munsell color chart) stages.

II. *Weight and shape of fruit*.—'FR3593W' average fruit weight is similar to the 'MD-2', and 'Champaka'; 'FR3593W' has a cylindrical shape.

III. *Ascorbic acid*.—'FR3593W' has a higher content of ascorbic acid than its relative *A. comosus* cv. 'EC', but similar to 'MD-2' variety.

IV. *Citric acid*.—'FR3593W' citric acid content is similar to 'MD-2'.

V. *Brix*.—The sugar content (measured as brix degrees) of 'FR3593W' is slightly higher to that found on 'MD-2'.

VI. *Age to forcing*.—'FR3593W' is vigorous and can reach forcing plant size 8-17 months after planting (shorter when using vegetative propagation material, and longer when starting with seed). Although plant development time to forcing depends on the size of planting material used and the desired plant weight at floral induction, the above figures are similar to those achieved by the 'MD-2' variety, which reaches an optimal forcing size in 8.5 months after planting when using vegetative propagation material.

VII. *Leaf spines*.—This characteristic is commonly used to differentiate pineapple plants from other varieties. The color of the leaf spines are as follows: Tip: dark green like MD-2 (8GY 5.8/3.2 in the Munsell color chart), base: dark green like MD-2 (8GY 5.8/3.2 in the Munsell color chart). 'FR3593W' does not have conspicuous or regular thorns on the leaf like its parental '1/2.63', although 'MD-2' often presents irregular thorns on the edges of the leaf blade as well.

VIII. *Fruit quality of 'FR3593W' when compared with other pineapple varieties*.—Most pineapple varieties grown worldwide are produced for local consumption, and very few are grown for international commercialization and global distribution. The fruit characteristics bred into 'FR3593W' were specifically chosen to comply with the strictest quality standards of export markets like those of North America, Europe, and Asia Pacific. As shown in Table 7, 'FR3593W' compares very favorably against 'MD-2', the pineapple variety that has achieved most notoriety to date in global markets.

TABLE 7

| Comparison of 'FR3593W' against other varieties on some of the most important characteristics relevant to fresh fruit destined for exportation. | | | | |
|---|---|---|---|---|
| Variety/ | # Of slips | | Fruit weight (g) | |
| Cultivar[11] | Average | Range | Average | Range |
| 'FR3593W'[1] | 0 | 0-1 | 1214 | 709-1863 |
| 'MD-2'[2] | 1.2 | 0-3 | 1820 | 1070-2560 |
| 'Morada'[3] | 7.57 | 4-9 | 1887 | 1566-2000 |
| 'Honey Gold' | 1.5 | 0-3 | 1033 | 450-1678 |

TABLE 7-continued

Comparison of 'FR3593W' against other varieties on some of the most important characteristics relevant to fresh fruit destined for exportation.

| | | | | |
|---|---|---|---|---|
| 'Champaka 153'(3) | 1.1 | | 1710 | 420-3010 |
| 'Champaka F152' | 1.5 | | 2328 | |
| 'CO-2'(4) | | 2-3 | 2059 | 1297-2590 |
| 'Singapore' | | 2-12 | 1000 | |
| 'Spanish'(5) | | | | |
| 'Sarawak'(5) | 0 | | | 2000-4000 |
| 'Mauritius'(5) | 0 | | | 500-1500 |
| 'Josephine'(6) | | | | 1100-1300 |
| 'Scarlett'(6) | | | | 1400-2000 |
| 'Red Spansh'(7) | | 1-3 | | 1200-2000 |
| 'T'ainung 11'(7) | 6.9 | | 991 | 733-1269 |
| 'Imperial'(8) | 9 | | 1792 | |
| 'Perolera'(8) | | 8-10 | 1800 | |
| 'Pernambuco'(9) | | | | 1000-1500 |
| 'Primavera'(9) | | 7-10 | 1300 | |
| 'Queen'(10) | 10 | | | 500-1000 |

| Variety/ | Ascorbic Acid (mg/100 ml) | | Citric Acid (mg/ml) | |
|---|---|---|---|---|
| Cultivar(11) | Average | Range | Average | Range |
| 'FR3593W'(1) | 38.95 | 28.46-60.85 | 0.64 | 0.27-0.83 |
| 'MD-2'(2) | 53.06 | 37.00-69.06 | 0.6 | 0.36-0.84 |
| 'Morada'(3) | 20.03 | 9.90-24.90 | 0.69 | 0.58-0.86 |
| 'Honey Gold' | 21.14 | 14.73-37.36 | 0.98 | 0.67-1.33 |
| 'Champaka 153'(3) | 12.91 | 8.10-17.72 | 0.72 | 0.54-0.90 |
| 'Champaka F152' | | | 0.73 | |
| 'CO-2'(4) | | 30.80-55.50 | | 0.42-0.91 |
| 'Singapore' | | | | 0.50-0.60 |
| 'Spanish'(5) | | | | |
| 'Sarawak'(5) | | | | 0.30-0.65 |
| 'Mauritius'(5) | | | | 0.40-0.60 |
| 'Josephine'(6) | | | | |
| 'Scarlett'(6) | | | | |
| 'Red Spansh'(7) | | | | |
| 'T'ainung 11'(7) | | 1.40-18.50 | 0.5 | 0.40-0.6 |
| 'Imperial'(8) | | | 0.62 | |
| 'Perolera'(8) | | 20.00-40.00 | 0.64 | |
| 'Pernambuco'(9) | | | | |
| 'Primavera'(9) | | | 0.51 | |
| 'Queen'(10) | 26 | | 0.56 | |

| Variety/ | °Brix | |
|---|---|---|
| Cultivar(11) | Average | Range |
| 'FR3593W'(1) | 15.09 | 13.3-17.9 |
| 'MD-2'(2) | 15.55 | 12.9-17.2 |
| 'Morada'(3) | 13.51 | 12.2-15.1 |
| 'Honey Gold' | 16.18 | 14.4-18.1 |
| 'Champaka 153'(3) | 14.33 | 11.6-17.0 |
| 'Champaka F152' | 14.97 | |

TABLE 7-continued

Comparison of 'FR3593W' against other varieties on some of the most important characteristics relevant to fresh fruit destined for exportation.

| | | |
|---|---|---|
| 'CO-2'(4) | | 15.0-16.7 |
| 'Singapore' | | 10.0-12.0 |
| 'Spanish'(5) | | |
| 'Sarawak'(5) | | 14.0-17.0 |
| 'Mauritius'(5) | | 15.0-17.0 |
| 'Josephine'(6) | | 17.0-22.0 |
| 'Scarlett'(6) | | 15.0-18.0 |
| 'Red Spansh'(7) | 12.00 | |
| 'T'ainung 11'(7) | 14.00 | 13.2-15.1 |
| 'Imperial'(8) | 15.80 | |
| 'Perolera'(8) | 13.10 | 14.0-16.0 |
| 'Pernambuco'(9) | | |
| 'Primavera'(9) | 13 | |
| 'Queen'(10) | | 14.0-16.0 |

(data for 'FR3593W' represent observations from the first plant evaluated when backcrossing 'MD-2' with 1/2.63 hybrid; data for 'MD-2' represents the average score for 'MD-2' variety in the region).

(1)FR3593W fruit harvested in Brazil.

(2)Pindeco's historical data base and monthly research report April 2001.

(3)Pindeco's fruit historical data base. Pindeco's forcing plant weight data base.

(4)Plant Pat. No. 8,863.

(5)Wee, Y. C. 1972. Some common pineapple cultivars of west Malaysia. Malays Pineapple pp 7-13.

(6)Bartholomew et al. 2003 The Pineapple, Botany, Production and Uses.

(7)Chang, Ching-Chyn, 1995 Tainung No. 13. Pineapple. Jour. Agric. Res. China 44(2): 287-296.

(8)Pinto da Cunha et al. 0 abacaxizeiro. Pineapple News Issue No 10 May 2003.

(9)Pinto da Cunha et al. 0 abacaxizeiro. Py et al. The pineapple Cultivation and uses.

(10)Del Monte pineapple germplasm collection database.

(11)Cultivars are unpatented unless indicated otherwise.

REFERENCES CITED

MATOS, A. P. (2008) Perdas causadas pela *F. guttiforme*. Available in https://www.embrapa.br/busca-de-publicacoes/-/publicacao/981520/situacao-e-perspectivas-da-abacaxicultura-no-amazonas.

MATOS, A. P. & JUNEGHANS, D. T. Variedades de abacaxi resistentes a *F. guttiforme*. 2006. Cruz das Almas, B A. Available in https://ainfo.cnptia.embrapa.br/digital/bitstream/item/42932/1/VARIEDADES-ABACAXI-ARISTOTELES.pdf.

Munsell Color chart for Plant Tissues. published by Munsell pilp Macbeth, a division of Kollmorgen Corporation, Baltimore, Md. USA.

What is claimed is:

1. A new and distinct *Ananas comosus* plant named 'FR3593W', as illustrated and described herein.

* * * * *